United States Patent [19]

Chases

[11] Patent Number: 4,991,572

[45] Date of Patent: Feb. 12, 1991

[54] LUMBAR TRACTION DEVICE

[76] Inventor: Ronald L. Chases, 621 Seabright La., Del Mar, Calif. 92075

[21] Appl. No.: 429,027

[22] Filed: Oct. 30, 1989

[51] Int. Cl.⁵ .......... A61F 5/04

[52] U.S. Cl. .......... 128/75; 128/78; 128/DIG. 20

[58] Field of Search .......... 128/75, 78, DIG. 20, 128/84 R, 68.1, 24.1

[56] References Cited

U.S. PATENT DOCUMENTS

| | | | |
|---|---|---|---|
| 437,822 | 10/1890 | Reach | 212/93 |
| 1,080,297 | 12/1913 | Pitts et al. | 128/75 |
| 1,116,773 | 10/1914 | West et al. | 128/75 |
| 1,646,590 | 10/1927 | Mildenberg | 128/DIG. 20 |
| 2,459,545 | 1/1949 | Schultz | 128/75 |
| 3,160,143 | 12/1964 | Gray | 128/75 |
| 3,548,819 | 12/1970 | Davis et al. | 128/DIG. 20 |
| 3,810,466 | 5/1974 | Rogers | 128/75 |
| 3,921,626 | 11/1975 | Neel | 128/75 |
| 4,135,503 | 1/1979 | Romano | 128/78 |
| 4,552,135 | 11/1985 | Racz et al. | 128/78 |
| 4,643,173 | 2/1987 | Bell et al. | 128/68.1 |
| 4,702,235 | 10/1987 | Hong | 128/68.1 |
| 4,756,306 | 7/1988 | Curlee | 128/DIG. 20 |

FOREIGN PATENT DOCUMENTS

| | | | |
|---|---|---|---|
| 1208656 | 9/1959 | France | 128/25 R |
| 1461408 | 11/1966 | France | 128/78 |
| 2611135 | 8/1988 | France | 128/75 |
| 660681 | 5/1979 | U.S.S.R. | 128/75 |
| 797664 | 1/1981 | U.S.S.R. | 128/75 |
| 1523 | of 1909 | United Kingdom | 441/108 |
| 702613 | 1/1954 | United Kingdom | 182/3 |

*Primary Examiner*—David A. Wiecking
*Assistant Examiner*—Tonya Lamb
*Attorney, Agent, or Firm*—Lewis E. Massie

[57] ABSTRACT

A lumbar traction harness, comprising a quarter section of an inflatable ring of a semi-circular cross-section with a manually controlled valve for adjusting the amount of air in the ring. A support strap is attached to one of two tapered ends of the ring with equalization rings on the external ends providing for suspending the ring while supporting a patient in a variety of orthopedically proven positions.

6 Claims, 3 Drawing Sheets

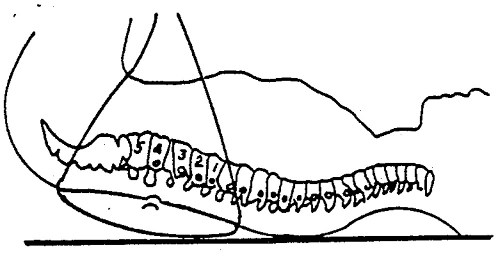
FIG. 8
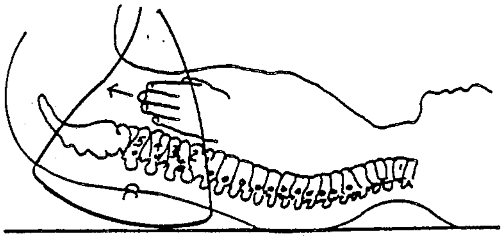
FIG. 9
FIG. 6
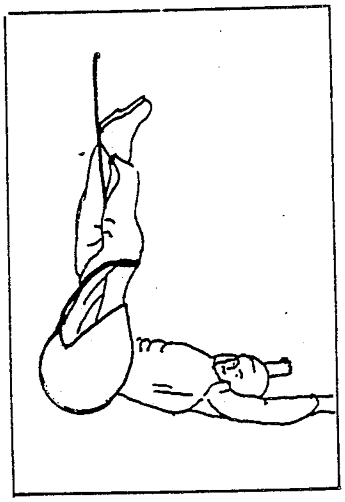
FIG. 7
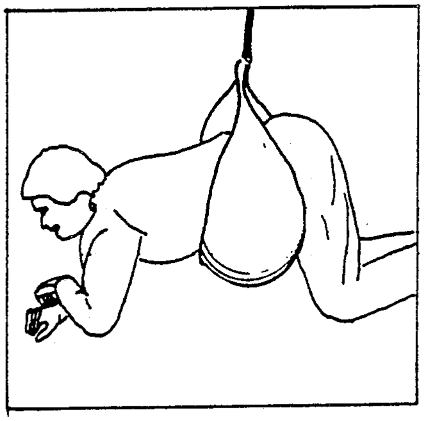
FIG. 10
FIG. 11
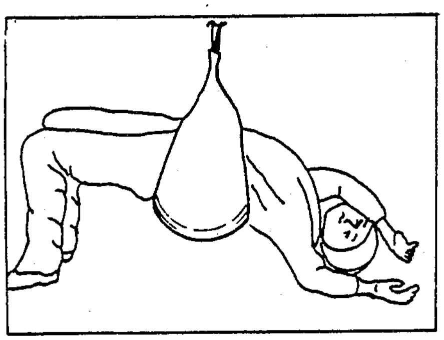

LUMBAR TRACTION DEVICE

BACKGROUND OF THE INVENTION

1. Field of the Invention

Back pain is one of the most common ailments affecting the adult population of the world. One often-used method for treating back pain is the use of traction. Traction is a way to stretch the body to relieve the pressure on the spine and can be an effective method of pain reduction.

Available traction devices range from cloth harnesses to belts and straps which utilize pulley and weight systems to stretch a patient.

2. Description of the Related Art

The prior art describes a multitude of belts designed to be applied to the upper portion of the human body. Some of the belts are designed for rescue work or body restraint and have been adapted, in some cases, to orthopedic therapy and are prescribed for treatment of specific cases.

Belts for restraint and rescue are described in patents issued to: Reach, U.S. Pat. No. 437,822; Forth British Pat. No. 1523; Pitts, U.S. Pat. No. 1,080,297; Schultz, U.S. Pat. No. 2,459,297; Stewart, British Pat. No. 702,613; Gray, U.S. Pat. No. 3,160,143; and Schulman, U.S. Pat. No. 3,948,541.

Belts designed for orthopedic therapy are described in patents issued to: West, U.S. Pat. No. 1,116,773; Kilmer, U.S. Pat. No. 4,135,503; Burton, U.S. Pat. No. 4,204,665; Gross, French Pat. No. 1,461,408.

SUMMARY OF THE INVENTION

The lumbar traction device is a harness that inflates from end to end completely encircling and semi-suspending the back pain patient in a variety of orthopedically proven positions. While in semi-suspension the gravitational pull on the patient's own body produces traction, releasing pressure and pain related to low back problems.

The simple flat belts and straps as well as cloth harnesses that are utilized to traction patients today tend to cut into the body and even slip off of the patient as tractive forces are applied. When a belt cuts into the body with force, the body tenses and the muscles shorten which is the exact opposite of the stretching traction tries to accomplish. Patient relaxation is the key to more effective traction and any assistance to patient comfort results in greater relaxation.

The lumbar traction harness overcomes currently used traction modalities in that it surrounds the patient with air-cushioned comfort while the patient is semi-suspended. (See FIG. 2, Page 13). This inflatable harness has a stop valve affixed to it that allows air in and out. Everyone is different as far as comfort needs and touch sensory so this valve allows the patient to adjust the air pressure while in traction for personal suitability. The release of air also lowers the patient into greater or lesser traction depending on the patient's individual needs.

Said harness is a bag shaped as the quarter section of a ring. Inside of the bag in the same shape as the bag and reaching from end to end, is an inflatable bladder. When inflated, this harness is changeable in shape from conforming to non-conforming depending on the amount of air inside. However, when the bodyweight load is placed on the harness, the harness conforms closely to the individual body shape: small, average, or large.

Currently used traction methods can supply only general traction to the spine. For example, oftentimes traction is applied with opposing belts that may traction a foot or more of the spine when the problem area may actually be quite small. A great deal of tractive force is required when generally tractioning a large area to effect a small spot increasing the likelihood of patient discomfort.

The lumbar traction device, when fully inflated, is cross-sectionally circular and smooth. This enables the patient, while in the low inverted traction position, to slide the harness along the spine while in traction. Through the feel of the placement of the harness, the patient can position said harness at the most effective spot for personal pain reduction. (See FIG. 9, Page 14). The attachment of a small isolating seam on the inside radius of said harness by the use of VELCRO, or hook and loop type fasteners, can further aid in pinpointing the traction to the exact problematic spinal segment. (See FIGS. 9*a* and 9*b*, Page 15).

This ability to pinpoint the traction overcomes the previous traction methods which utilize belts and straps that are immovable and apply a non-specific stretch.

These pains in the low back are unique to the individual sufferer. Standard traction techniques will work for some, but oftentimes the pain is so intense that much of the trunk of the body as well as the legs and feet hurt. For this type of pain, climbing onto a table for standard belttype tractive force can easily aggravate the condition.

Different body positions and body dynamics also affect back pain. For years doctors and therapists have used flexion, extension, and manipulation to treat back pain, but standard traction tables are very limited as far as body positioning while in traction.

The simple design of the lumbar traction device allows for traction in a variety of body positions depending on the back pain problem and which position relieves the pain most effectively. For example, the upright flexed position is for more acute pain because of the ease of obtaining the position. The hands and knees position is used by patients who are in much pain that they cannot walk. (See FIG. 10, Page 16). The supine extended position is for patients with an anterior disc bulge. (See FIG. 11, Page 16). The low inverted position allows a more chronic patient to slide the bubble to the exact spot where traction is needed. (See FIG. 9, Page 14).

This VELCRO on the inside radius of said lumbar traction harness can also be used to attach a pocket for heat or cold, vibration electro-stem, or accupressure pads to be used simultaneously with traction. Until now these modalities had to be used separately of traction.

Finally, in the low inverted position manipulation can be accomplished simultaneously with traction by simply pushing one side of the harness and pulling the other and then reversing the procedure allowing the patient's own bodyweight to assist in the procedure. Until the present invention, manipulation relied on the bodyweight of the medical practitioner to assist in manipulating the patient.

The ends of said inflatable harness are tapered with equalization rings on either end and a long strap on one of the ends. The long strap goes through the ring on the opposite end and back through the ring on the end it originates from. The end of the strap is then secured above to a chin bar. This type of fastening assembly makes the harness gravitationally cinch the patient in safely as the bodyweight is loaded. There is less chance of slippage with this type of fastening technique and it allows easy exit as bodyweight is removed from the harness for the more acute patient where fumbling with a buckle-type assembly may increase pain. The equalization rings on either end of said harness ensure air pressure equalization around the patient for comfort as gravitational loading takes place.

The lumbar traction device has been successfully tested on a large number of back pain patients and has verified an acceptable need for the device.

BRIEF DESCRIPTION OF THE DRAWINGS

FIG. 6 shows the upright flexed position.

FIG. 7 shows the modified low inverted position.

FIG. 8 shows the isolating seam in use.

FIG. 9 shows how to move the isolating seam.

FIG. 10 shows the hands and knees flexed position.

FIG. 11 shows the supine extended position.

DETAILED DESCRIPTION OF THE PREFERRED EMBODIMENT

Figure 1:
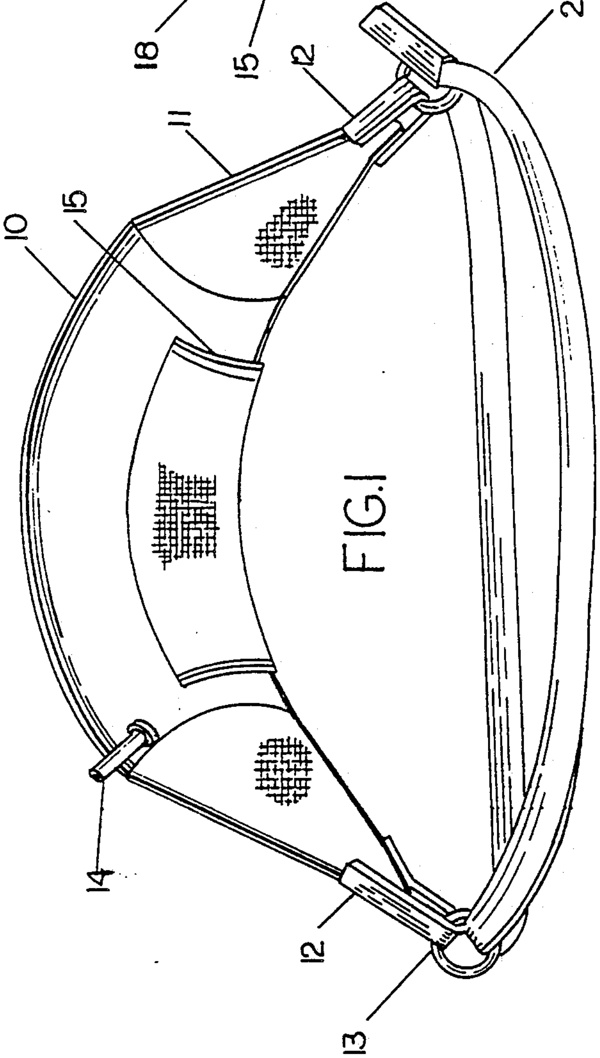
FIG. 1 is a front perspective view of the lumbar traction device.

Referring to FIG. 1, a soft, pliable bag 10 enclosing an end-to-end inflatable bladder, in the form of a quarter section of a ring of circular cross-section is shown with air control valve 14. The support strap 21 with equalization rings 13 are shown attached to loops 12 on the tapered ends 11 of the traction device 10. A rectangular strip of VELCRO 15 is attached to the inside circumference of the device 10 for attaching or removing the isolating seam and accessory pocket as needed.

Figure 2:
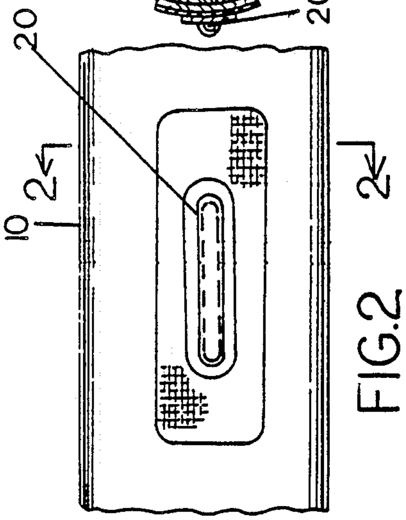
FIG. 2 is a detailed front view of the isolating seam.
Figure 2:
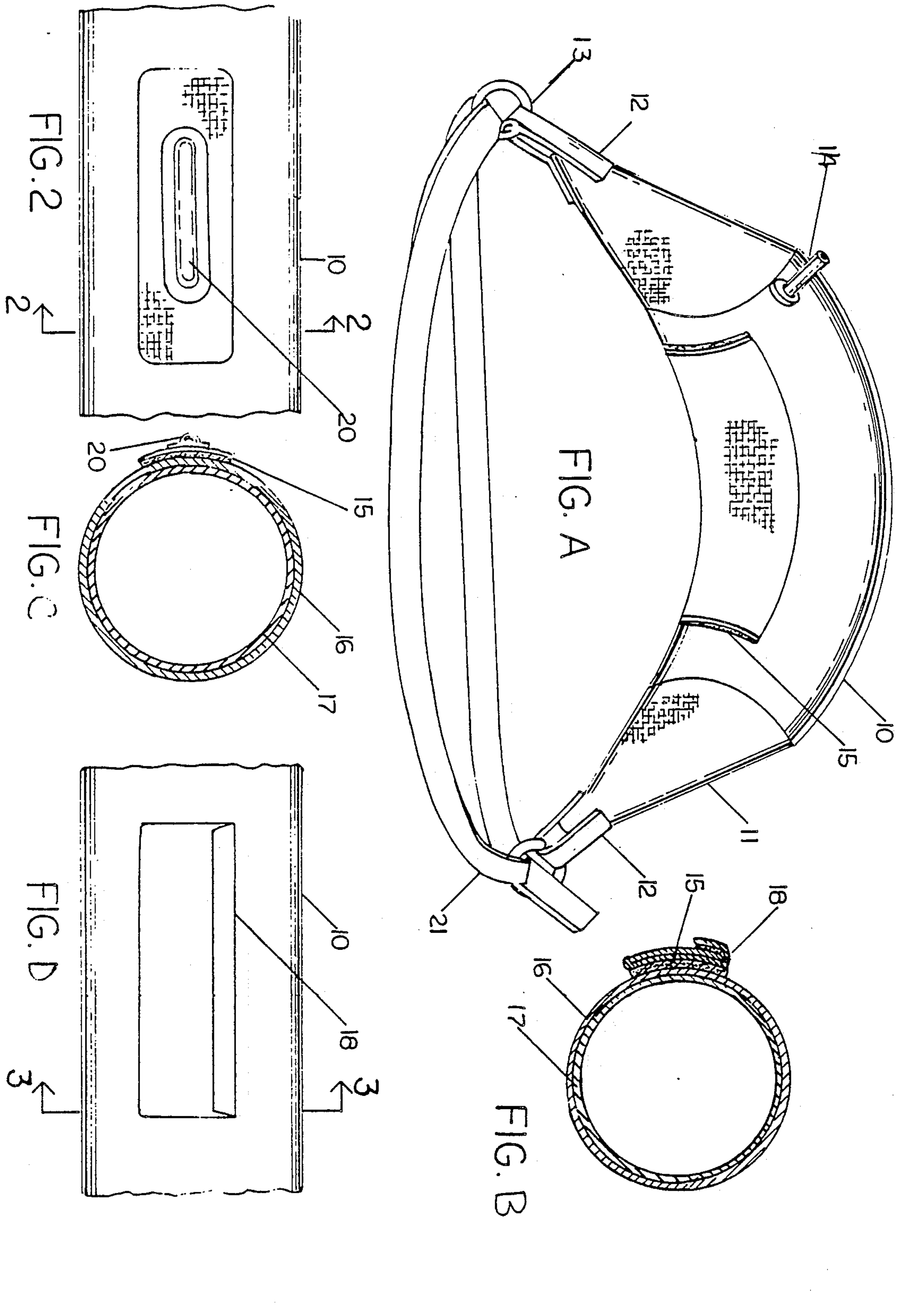

The detailed view of FIG. 2 shows the isolating seam 20 attached by VELCRO to the inside radius of the lumbar traction device 10.

Figure 3:
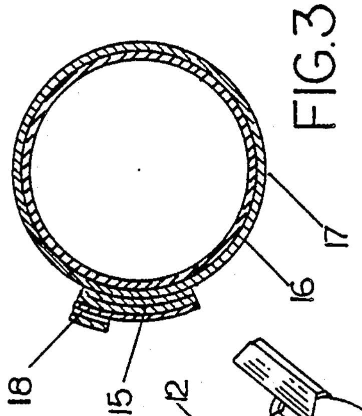
FIG. 3 is a sectional view through 2—2 of FIG. 2.

The sectional view of FIG. 3 taken through 2—2 of FIG. 2 shows an inner bladder 17 inside the outer covering 16 with the isolating seam 20 attached to the VELCRO strip 15.

Figure 4:
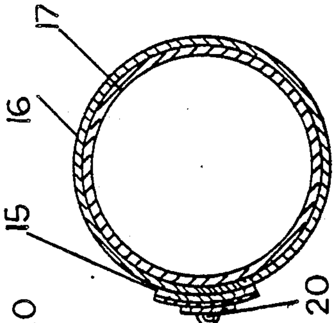
FIG. 4 is a front view of the accessory pouch.

FIG. 4 is a detailed view of the accessory pouch 18 attached by VELCRO to the inside radius of the lumbar traction device 10.

Figure 5:
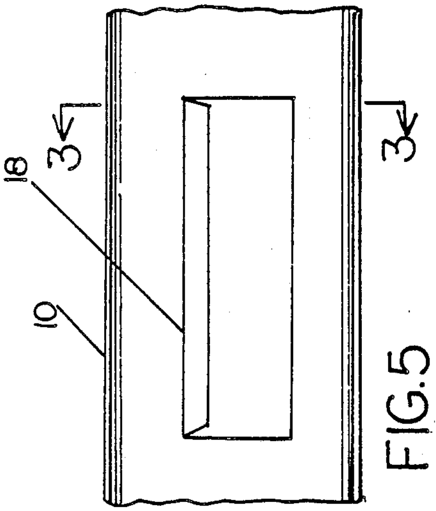
FIG. 5 is a sectional view through 3—3 of FIG. 3

FIG. 5 is a sectional view taken through 3—3 of FIG. 4 showing the accessory pouch 18 attached by the VELCRO strip 15 to the outer covering 16 encasing the inner bladder 17.

Back Bubble Instructions, Method of Operation:

The chin bar is extended to either side of the doorway to be used, making sure that the doorway is a safe width. (There is a warning sticker on the inside bar of the chin bar showing how far it can safely be extended). The chin bar is installed by attaching two brackets to either side of a doorway. With an average door jamb, about 6 feet, 8 inches high, 3 inches from the top of the door jamb will be the top point of the bracket. For higher doorways approximately 6 feet, 5 inches from the floor will be the highest point on the bracket. The Back Bubble can also be hung by a hook in a beam or a sturdy rope or chain.

The back bubble is then inflated. The tip of the valve is depressed and air blown into it. For comfort adjustment the bubble is deflated by depressing the valve tip while avoiding covering the hole where air escapes.

To raise and lower the Back Bubble, the metal lip is raised at the bottom of the three-bar slide (the small rectangular piece below the spring) until it is parallel with the floor. Holding it in this position the strap is pulled through this three-bar slide, thus changing the height of the Back Bubble.

When the Back Bubble is hanging free from the chin bar, the crease by the valve on the bubble should be in approximately the center of the bubble from one end to the other.

Upright flexed position (Pictured in FIG. 6)

To have the back bubble at the proper height for the patient in the upright flexed position, the unit is inflated so when it hangs it forms a heart shape. The height of the back bubble is adjusted so that the point of the heart is at mid thigh of the patient or about 8 inches below the greater trochanter. (With every patient exact height will vary according to individual patient comfort, but this is a good starting point.) The patient puts their head and arms through the inflated bubble. The bubble will now encircle the body with the valve on the patient's right side away from the body. Next, the patient steps forward from under the spring about one foot and the front of the Back Bubble is pushed down under the rib cage, and the bubble is grasped and pulled in under the rib cage. The crease that is centered on the bubble also should be centered on the patient. Holding on tightly, the patient assumes a sitting position. If bubble is too tight, some air is let out by depressing the valve tip (without covering the hole when depressing the valve). If the patient wants to increase the traction, the feet are moved forward from under the knees 1 inch at a time, which takes the weight off the feet and increases traction. Another way to increase traction is with the feet slightly forward from below the knees in the upright flexed position, the patient pushes straight back until legs are straight then rolles the upper part of the body forward over bubble. The upright flexed position is great for relief of sciatic pain. A variation of this position can be achieved with the bubble behind the patient's back.

Modified low inverted position (Pictured in FIG. 7)

The free-hanging bubble is lowered until it is about 6 inches off the ground. The patient puts the bubble around the small of the back, on the crest of the hips, so that the valve is just behind right buttock. In this position the metal rings are in front. The bubble is cinched in tightly so that the metal ring that the strap goes through is centered on the body. The strap is grasped by the patient with the left hand directly in front of ring. This keeps it cinched tightly. The strap is grasped with the right hand just beneath the metal adjustment slide. (Two straps should be grasped for safety—the main strap and the excess that runs through the slide.) Grasping high and low the patient steps under the spring and lower himself gently down onto the bubble. The bubble should still be on the crest of the hips. Next, the patient slides his top hand down to the bottom hand and in one smooth motion, brings his feet up, around and in front of the strap, then drops his upper body down. NOTE: The patient should bring his feet up and drop the upper body down at the same time to avoid extension, unless extension is desirable. When the patient rolls into position, as the patient's feet go up, the therapist places one foot lightly on the bubble directly under the patient's tailbone to stabilize the bubble.

To pinpoint the traction: While in position the patient places his hands on both sides of the bubble right next to his hips and pushes the bubble down his back 1 inch at a time to pinpoint the relief. If sliding the bubble is difficult, the patient thrusts his hips forward taking the weight off of the bubble; now the bubble will be easier to move. The point where the lumbar traction device touches the patient's body determines which spinal segment is tractioned the most. The isolating seam further pinpoints the traction. In FIG. 8 the most tractioned spinal segment is between numbers 3 and 4, however if the problem spinal area is between numbers 4 and 5 the lumbar traction device is pushed as in FIG. 9 to apply specific traction to the area.

Hands and knees flexed position (Pictured in FIG. 10)

The height of the free-hanging bubble is the same as with the low inverted position. The bubble is placed around the patient in front, the same as the upright position but with the bubble lower, around the hips. The patient assumes a hands and knees position with the bubble low around the hips and walks hands and knees away from the spring until the strap is tight. The patient then leans forward and downward onto forearms and pushes forward with toes to increase traction. NOTE: The bubble should be pushed way down on hips and the strap should be tight. To make it easier to push the unit down on hips let air out of the bubble.

Supine extended position (Pictured in FIG. 11)

The height of the bubble hanging free should be the same as in the upright flexed position. The bubble is placed around the patient's lower back at about the crest of the hips. Next, the bubble is cinched in tightly with the rings in front, then the body is lowered gently on the bubble while holding onto the strap. Once the patient's body weight is totally on the bubble, the patient lets go and extends as shown in FIG. 11. NOTE: The bubble can be moved to different areas of the back to isolate a specific area for extension.

I claim:

1. An end-to-end inflatable lumbar traction harness for encircling and semi-suspending a patient in a variety of orthopedic positions comfortably while the gravitational pull on the patient's own body releases pressure on the spine for immediate back pain relief wherein the improvement comprises:

(a) a bag shaped as the quarter section of a ring with a circular cross-section;
(b) said bag enclosing an airtight bladder, which completely fills the bag from end-to-end when inflated;
(c) said bag having affixed to it a stop valve to adjust the air pressure around the patient for personalized comfort while in suspension and to let air out of the bladder for lowering the patient into different body positions or into increased or decreased traction;
(d) said bag, when inflated having a smooth, curved inside surface that can be moved along the spine by the patient while in traction to position the harness for maximum pain relief;
(e) said bag having means for pinpointing the traction force and for assisting in opening the spinal segments, said means comprising an isolating seam; and
(f) said bag having hook and loop type fasteners on the inside surface for the attachment of the above means.

2. An end-to-end inflatable lumbar traction harness for encircling and semi-suspending a patient in a variety of orthopedic positions comfortably while the gravitational pull on the patient's own body releases pressure on the spine for immediate back pain relief wherein the improvement comprises:

(a) a bag shaped as the quarter section of a ring with a circular cross-section;
(b) said bag enclosing an airtight bladder, which completely fills the bag from end-to-end when inflated;
(c) said bag having affixed to it a stop valve to adjust the air pressure around the patient for personalized comfort while in suspension and to let air out of the bladder for lowering the patient into different body positions or into increased or decreased traction;
(d) said bag, when inflated having a smooth, curved inside surface that can be moved along the spine by the patient while in traction to position the harness for maximum pain relief;
(e) said bag having means for providing accupressure, vibration, heat or cold, said means comprising a pocket containing one of the above and placed on the inside surface of said bag; and
(f) said bag having hook and loop type fasteners on the inside surface for the attachment of the above means.

3. A method for applying traction comprising the steps of:

(a) providing a traction device comprising
  (1) a bag shaped as the quarter section of a ring with a circular cross-section;
  (2) said bag enclosing an airtight bladder, which completely fills the bag from end-to-end when inflated;
  (3) said bag having affixed to it a stop valve to adjust the air pressure around the patient for personalized comfort while in suspension and to let air out of the bladder for lowering the patient into different body positions or into increased or decreased traction;
  (4) said bag, when inflated having a smooth, curved inside surface that can be moved along the spine by the patient while in traction to position the harness for maximum pain relief;
(b) suspending the traction device from above by a strap with the bottommost point of the bag approximately at mid thigh of the patient;
(c) placing the patient's head and arms through the bag so that the patient is encircled and then having the patient:
  (1) step forward from under the point of suspension about 1 foot;
  (2) push the bag under the rib cage;
  (3) assume a sitting position with the upper body at least minimally tilted over the bag and with the patient's trunk remaining under the point of suspension; and
(d) adjusting the feet forward from under the knees incrementally to take weight off of the feet and increase traction to the desired amount.

4. A method for applying traction comprising the steps of:

(a) providing a traction device comprising
  (1) a bag shaped as the quarter section of a ring with a circular cross-section;

(2) said bag enclosing an airtight bladder, which completely fills the bag from end-to-end when inflated;

(3) said bag having affixed to it a stop valve to adjust the air pressure around the patient for personalized comfort while in suspension and to let air out of the bladder for lowering the patient into different body positions or into increased or decreased traction;

(4) said bag, when inflated having a smooth, curved inside surface that can be moved along the spine by the patient while in traction to position the harness for maximum pain relief;

(b) suspending the traction device from above by a strap with the bottommost point of the bag approximately 6 inches above the floor;

(c) placing the bag around the small of the patient's back, on the crest of the hips and cinching the bag tightly around the patient and then having the patient;

(1) grasp the strap with hand, one hand being higher than the other;

(2) lower his weight down onto the bubble;

(3) slide upper hand down to lower hand;

(4) in one motion bring feet up, around and in front of the strap and drop upper body down; and (d) sliding bubble along spine to pinpoint the traction.

5. A method for applying traction comprising the steps of:

(a) providing a traction device comprising (1) a bag shaped as the quarter section of a ring with a circular cross-section;

(2) said bag enclosing an airtight bladder, which completely fills the bag from end-to-end when inflated;

(3) said bag having affixed to it a stop valve to adjust the air pressure around the patient for personalized comfort while in suspension and to let air out of the bladder for lowering the patient into different body positions or into increased or decreased traction;

(4) said bag, when inflated having a smooth, curved inside surface that can be moved along the spine by the patient while in traction to position the harness for maximum pain relief;

(b) suspending the traction device from above by a strap with the bottommost point of the bag approximately 6 inches above the floor;

(c) placing the bag around the patient with the center of the bag anteriorly placed on the patient and around the hips and then having the patient:

(1) assume a position on hands and knees with the bag still around the hips;

(2) walk hands and knees away from the point of suspension until the strap is tight;

(3) lean forward and downward onto forearms; and (d) pushing forward with toes to increase traction.

6. A method for applying traction comprising the steps of:

(a) providing a traction device comprising (1) a bag shaped as the quarter section of a ring with a circular cross-section;

(2) said bag enclosing an airtight bladder, which completely fills the bag from end-to-end when inflated;

(3) said bag having affixed to it a stop valve to adjust the air pressure around the patient for personalized comfort while in suspension and to let air out of the bladder for lowering the patient into different body positions or into increased or decreased traction;

(4) said bag, when inflated having a smooth, curved inside surface that can be moved along the spine by the patient while in traction to position the harness for maximum pain relief;

(b) suspending the traction device from above by a strap with the bottommost point of the bag approximately at mid thigh of the patient;

(c) placing the bag around the patient's lower back with the center of the bag posterior and about the crest of the hips and cinching the bag tight and then having the patient:

(1) grasp the strap with hands;

(2) lower body weight totally on the bubble;

(3) let go of the strap and extend hands over the head;

(d) sliding the bag along the spine to pinpoint traction.

* * * * *